(12) United States Patent  (10) Patent No.: US 7,874,199 B2
Chaudoreille et al.  (45) Date of Patent: Jan. 25, 2011

(54) DENSITY AND VISCOSITY SENSOR

(75) Inventors: Francois Chaudoreille, Poissy (FR);
Alfred Permuy, Rueil Malmaison (FR);
Eric Donzier, Bercheres sur Vesgre (FR)

(73) Assignee: Schlumberger Technology Corporation, Sugar Land, TX (US)

( * ) Notice: Subject to any disclaimer, the term of this patent is extended or adjusted under 35 U.S.C. 154(b) by 411 days.

(21) Appl. No.: 12/097,901

(22) PCT Filed: Dec. 27, 2006

(86) PCT No.: PCT/EP2006/012652
§ 371 (c)(1),
(2), (4) Date: Jun. 18, 2008

(87) PCT Pub. No.: WO2007/077038
PCT Pub. Date: Jul. 12, 2007

(65) Prior Publication Data
US 2008/0257036 A1 Oct. 23, 2008

(30) Foreign Application Priority Data
Dec. 30, 2005 (EP) .................................. 05292827

(51) Int. Cl.
*G01N 9/10* (2006.01)
*G01N 11/16* (2006.01)
(52) U.S. Cl. .................... 73/32 A; 73/54.26
(58) Field of Classification Search ............ 73/32 A, 73/54.24, 54.26, 54.27, 290 V
See application file for complete search history.

(56) References Cited

U.S. PATENT DOCUMENTS

| 4,383,443 | A | * | 5/1983 | Langdon | 73/290 V |
| 4,594,584 | A | * | 6/1986 | Pfeiffer et al. | 340/620 |
| 5,323,638 | A | | 6/1994 | Langdon et al. | |
| 6,389,891 | B1 | | 5/2002 | D'Angelico et al. | |
| 6,494,079 | B1 | | 12/2002 | Matsiev | |
| 6,644,116 | B2 | * | 11/2003 | Getman et al. | 73/290 V |
| 6,845,663 | B2 | * | 1/2005 | Lopatin et al. | 73/290 V |
| 6,938,475 | B2 | * | 9/2005 | Lopatin | 73/290 V |
| 7,043,981 | B2 | * | 5/2006 | Kuhny et al. | 73/290 V |

FOREIGN PATENT DOCUMENTS

| EP | 0282251 | 9/1988 |
| WO | 2004086002 | 10/2004 |
| WO | WO2005114138 | 12/2005 |

* cited by examiner

*Primary Examiner*—John Fitzgerald
(74) *Attorney, Agent, or Firm*—Matthias Abrell (57) ABSTRACT

A density and viscosity sensor for measuring density and viscosity of a fluid, and method for measuring, are presented herein. The sensor comprises a resonating element, and actuating/detecting element, a connector and a housing. The actuating/detecting element is positioned within a chamber defined by the housing so as to be isolated from the fluid. The resonating element is arranged to be immersed in the fluid, and has a shape defining a first resonance mode and a second resonance mode characterized by different resonance frequencies and different quality factors. The first resonance mode is adapted to move a volume of fluid, and the second resonance mode is adapted to shear a surrounding fluid.

17 Claims, 8 Drawing Sheets

DENSITY AND VISCOSITY SENSOR

FIELD OF THE INVENTION

The invention relates to a sensor for measuring density and viscosity of a fluid. The sensor is based on the use of mechanical elements put into vibration in the fluid to be measured.

The invention is applicable to density and viscosity measurements in the oilfield industry, in the chemical industry, in the food industry, etc. . . .

BACKGROUND OF THE INVENTION

The density is a measure of a mediums mass per unit of volume. The SI unit of density is the kilogram per cubic meter ($kg/m^3$). As examples, at standard temperature and pressure condition, the density of water is $1000\,kg/m^3$, of ethyl alcohol is $790\,kg/m^3$, respectively.

Viscosity is a measure of the resistance of a fluid to deformation. Viscosity describes a fluid internal resistance to flow and may be thought of as a measure of fluid friction. The SI physical unit of dynamic viscosity is the Pascal second (Pa·s). The cgs physical unit for dynamic viscosity is the poise (P). It is more commonly expressed, particularly in ASTM standards, as centipoise (cP). As example, water has a viscosity of 1.0 cP (at 20° C.).

It is known from patent document EP0282251, a transducer for measuring density or viscosity of fluid. The transducer comprises two parallel tines extending from a common yoke, forming a tuning fork adapted to be immersed in the fluid. The tines are excited to vibrate resonantly and in antiphase by one or more piezoelectric exciting elements, which are housed in one or more cavities within the tines or the yoke. The vibrations are sensed by one or more similarly-housed piezoelectric sensing elements.

This transducer has a typical size of several centimeters requiring a bulky and expensive sensor housing. This leads to a highly intrusive measuring device preventing its use in small sample chambers or small pipes. Accuracy of such device is limited by pressure and temperature effects on the sensor materials requiring adding complementary pressure and temperature sensors for corrections. Operation at high pressure and high temperature is also very difficult to implement due to the large size and due to the piezoelectric transducer elements implementation inside the sensor housing. Further the sensor geometry does not allow to align the sensing element with the flow leading to large measurement perturbations at high fluid velocities.

The patent application EP05290502.3 filed on 4 Mar. 2005 discloses a miniaturized density and viscosity sensor. This sensor requires additional temperature and pressure sensor for correcting the effect of temperature and pressure variation on the frequency and quality factor impacting density and viscosity measurements. The membrane movement generates a large acoustic signal in the fluid that may induce perturbation signal by microphonic effect. The piezoelectric element may be submitted to high stress at high pressure. The excitation detection scheme is based on frequency sweep which is time consuming in the determination of density and viscosity.

SUMMARY OF THE INVENTION

One goal of the invention is to propose a sensor for measuring density and viscosity of a fluid that overcomes at least one of the shortcomings of the prior art.

According to a first aspect, the invention relates to a density and viscosity sensor for measuring density and viscosity of fluid comprising:

a resonating element arranged to be immersed in the fluid,
an actuating/detecting element coupled to the resonating element,
a connector for coupling to the actuating/detecting element,
a housing defining a chamber isolated from the fluid, the housing comprising an area of reduced thickness defining a membrane separating the chamber from the fluid, the membrane having a thickness enabling transfer of mechanical vibration between the actuating/detecting element and the resonating element,
the actuating/detecting element is positioned within the chamber so as to be isolated from the fluid and mechanically coupled to the membrane),
the resonating element arranged to be immersed in the fluid is mechanically coupled to the membrane,
the resonating element has a shape defining a first resonance mode and a second resonance mode characterized by different resonant frequencies and different quality factors, the first resonance mode moving a volume of fluid, the second mode shearing a surrounding fluid.

The resonating element is mechanically coupled to the membrane by a mechanical coupling element and may be:

a beam, substantially straight, attached at one end to the coupling element and comprising, at the other end, a spherical mass, or
a non-symmetrical U beam comprising a spherical mass suspended at one end,
a beam, substantially straight, attached at its center to the coupling element and comprising, at the each end, a spherical mass, or
a straight connecting part attached to the coupling element and comprising, at one end, a paddle shape beam, or
a straight connecting part attached to the coupling element and comprising, at each end, a first and a second paddle shape beam, or
a beam, substantially straight, attached at one end to the coupling element and comprising, around the other end, a plate, or
a beam, substantially straight, attached at one end to the coupling element and comprising, around the other end, a tube portion.

The resonating element may comprise at least a part of the beam aligned with the fluid flow direction.

According to further aspects the invention, the area of reduced thickness may forms a cavity in which the actuating/detecting element is secured.

The actuating/detecting element may comprise at least one piezoelectric element.

One of the piezoelectric element may comprise a first and a second side, the first side being coupled to the connector by a connecting wire, the second side being electrically coupled to the membrane.

The piezoelectric element may pushed against the membrane through a compression assembly screwed into the cavity, said compression assembly comprising a hole for coupling to the connecting wire. The compression assembly may comprise a plug, a screwing plug and a supporting part.

The sensor further comprises an electronic arrangement for driving the actuating/detecting element from an actuating mode into a detecting mode and vice-versa.

According to another aspect, the invention relates to a method for measuring density and viscosity of a fluid comprising the steps of:

a) applying an excitation signal to a resonating arrangement comprising an actuating/detecting element and a resonating element arranged to be immersed in the fluid, b) detecting a reception signal provided by the resonating arrangement, c) determining an in-phase sensor actual response and a quadrature sensor actual response based on the reception signal detected, d) calculating an in-phase sensor model response and a quadrature sensor model response based on an initial resonant frequency and an initial quality factor of the resonating element, e) comparing the in-phase sensor model response to the in-phase sensor actual response, and the quadrature sensor model response to the quadrature sensor actual response by determining an associated correlation coefficient, f) repeating the calculating step and the comparing step with a modified resonant frequency and a modified quality factor and memorizing a determined number of resonant frequency, quality factor and associated correlation coefficient, and g) determining a resulting resonant frequency and a resulting quality factor of the resonating element in the fluid based on the determined number of associated correlation coefficient, wherein the resulting resonant frequency and the resulting quality factor of the resonating element are determined according to a first resonance mode and a second resonance mode of the resonating element characterized by a different first and second resonant frequency and a different first and second quality factors, the first resonance mode moving a volume of fluid, the second mode shearing a surrounding fluid.

The excitation signal may be a broadband excitation signal including the different resonant frequencies or the excitation signal may swept a range of frequency including the different resonant frequencies.

The method further may comprise the step of determining density and viscosity of the fluid based on the first and second resonant frequency and the first and second quality factors and a plurality of fitting parameters that are determined by measuring the resonance frequencies and quality factors in fluids of known density and viscosity. Advantageously, the comparison and resonant frequency/quality factor determination steps are based on a parametrical identification.

Consequently, the sensor of the invention enables overcoming the temperature and pressure effect on the beam material. Using at least two vibration modes with different coupling equations with the fluid enables computation of density and viscosity independently from pressure and temperature. Two sensors each using a vibrating mode with different coupling with the fluid may also be possible.

The use of a high piezoelectric disk to membrane surface ratio, enables operation of the sensor at high pressure.

The density and viscosity sensor of the invention is accurate over an extended pressure and temperature range, in particular the sensor is compliant with high pressure and high temperature operation (e.g. up to 30 Kpsi and 200° C.).

The sensor of the invention improves greatly the displacement to volume ratio allowing efficient resonator excitation without generating acoustic wave in the fluid, thus overcoming the microphonic effect.

Finally, the measurement method of the invention allows a drastic reduction of the measurement time by using a broadband excitation signal covering the full range of useful frequency.

BRIEF DESCRIPTION OF THE DRAWINGS

The present invention is illustrated by way of examples and not limited to the accompanying figures, in which like references indicate similar elements.

DETAILED DESCRIPTION OF THE INVENTION

FIGS. 1 to 22 show the density and viscosity sensor 1 of the invention.

Figure 1:
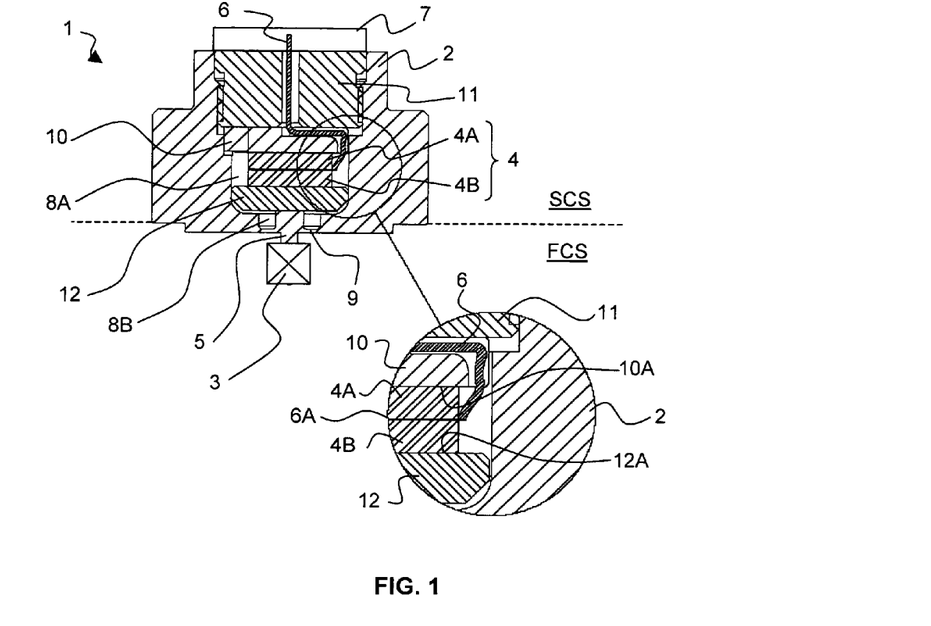
FIG. 1 is a cross-section view and an enlarged cross-section view part schematically showing a sensor for measuring density and viscosity of a fluid according to any one of the embodiments of the invention.

FIG. 1 is a cross-section view in a sensor 1 which may be any one of the possible sensor embodiments 1A, 1B, 1C, 1D, 1E, 1F and 1G. For clarity purpose, this Figure also shows a magnified portion of a piezoelectric element connection area.

The density and viscosity sensor 1 comprises a housing 2. The sensor comprises a resonating element 3. In FIG. 1, the resonating element 3 which may have various shapes, that will be described in more details hereinafter, is symbolized by a crossed rectangle.

The housing 2 may further comprise a connector 7 (for clarity purpose, the connector 7 is not shown in details). The connector 7 may be a standardized coax connector, a multi-sockets connector or any other connector adapted to a particular application. The housing 2 may comprise a peripheral groove (not shown) for receiving an O-ring type sealing (not shown). Any other sealing may be convenient provided that the sealing 15 separates a fluid contacting side FCS from the sensor connecting side SCS.

In the particular embodiments described, the mechanical coupling element 5 constitutes an integral part with the housing. However, it will be apparent for a person skilled in the art that the mechanical coupling element 5 may constitute an integral part with the resonating element or may be an additional part coupled to the housing and to the resonating element. The function of the mechanical coupling element is to mechanically couple the housing 2 to the resonating element so that vibration can be transmitted through it. Another function is to position the resonating element into the fluid to be measured, so that the resonating element is surrounded by said fluid or totally immersed in said fluid. The resonating element and the housing integral or not with the coupling element 5 may be assembled together (e.g. by any appropriate welding, gluing, brazing etc. technique).

The housing 2 comprises a housing interior part defining a chamber 8A. The housing 2, in the chamber side, comprises a cavity 8B. The cavity 8B defines an area where the housing has a reduced thickness defining a membrane 9 between the chamber 8A and the fluid contacting side FCS. The coupling element 5 is positioned onto the membrane 9. Preferably, the coupling element 5 is positioned at sensibly a center point on the membrane. The chamber 8A may be filled with a material. Advantageously, the material is a vibration absorbing material (e.g. gas, oil, gel, etc. . . . ). The vibration absorbing material enables to reduce perturbation due to parasitic vibration modes of the housing itself.

An actuating/detecting element 4, for example a piezoelectric element 4A, 4B is positioned in the cavity 8B. The piezoelectric element comprises one disk or a stack of at least two disks (e.g. piezoceramic disks) working in thickness mode and maintained under compression through a compression assembly detailed hereinafter. In the case of an odd number of piezoceramic disk elements, an extremity of the stack should be isolated from the housing.

The resonating element is coupled to the housing 2 and to the actuating/detecting element 4 by a mechanical coupling element 5 and a supporting part 12 The mechanical coupling element 5 supports on one side the resonating element 3 and on the other side the supporting part 12. The supporting part enables homogenizing mechanical stress at contact point with the actuating/detecting element. Alternatively, the supporting part 12 may not be present so that the actuating/detecting element 4 directly contacts the coupling element 5. The membrane 9 allows efficient transmission of mechanical signal between the actuating/detecting element 4 and the resonating element 3 while ensuring hermetically separating the fluid contacting side FCS from the cavity 8B.

The sensor comprises a plug 10 and a screwing plug 11 screwed into the chamber 8A for applying and compressing the piezoelectric element 4 onto the membrane 9. Alternatively, the screwing plug 11 may be screwed into the cavity 8B. The screwing plug 11 comprises an appropriate hole for the passage of the connecting wire 6 at sensibly the screwing plug center. The plug 10 enables application of the piezoelectric element onto the membrane when the screwing plug 11 is screwed. The plug 10 lets a passage for the connecting wire 6 from the screwing plug center to the piezoelectric element. One side of the piezoelectric element is coupled to the connector (not shown) by the connecting wire 6. The other side of the piezoelectric element 4 contacts the membrane 9. A supporting part 12 may be positioned between the plug 10 and the support element 5. The supporting part 12 constitutes a mechanical interface between the support element 5 and the piezoelectric element 4. Preferably, it may not contact the bottom of the chamber 8A and may slide within the chamber 8A. Thus, the mechanical vibrations are efficiently transferred between the resonating element 3 and the piezoelectric element 4 via the membrane 9 and the supporting part 12.

Generally, high levels of mechanical stress on common piezoelectric elements not only causes material damages (cracks) but drastically reduces piezoelectric efficiency making actuation detection impossible at very high pressure. With the sensor of the invention, the surface ratio between the membrane 9 and the piezoelectric element 4 reduces stress applied to the piezoelectric element by fluid pressure, enabling operation of the sensor at very high pressure.

Typically, a piezoceramic disk comprises a metal layer deposited on both sides of the disk. The electrical coupling may be easily obtained by manufacturing all sensor parts except piezoceramic disk stack out of metal and by mechanically securing the sensor assembly. The sensor can therefore be operated by applying voltage between the connecting wire 6 and the housing. As an alternative not shown, when the housing must be electrically isolated from electronics part, the plug 10 and supporting part 12 can be made of an insulating material and a second wire passed through the plug 10.

Thus, gluing or brazing the piezoelectric element onto the membrane can be avoided. Advantageously, the piezoelectric element 4 comprises two superposed piezoelectric elements 4A and 4B coupled to each other through a thin metal disk 6A connected to the connecting wire 6. The first piezoelectric element 4A is also coupled to the plug 10 by a second conductive layer 10A. The second piezoelectric element 4B is also coupled to the supporting part 12 by a third conductive layer 12A. The first piezoelectric element 4A has an inversed polarization state relatively to the second piezoelectric element 4B. The piezoelectric elements are mainly working in compression. Thus, the two superposed piezoelectric elements 4A and 4B may be excited by an appropriate electrical signal applied between on the one side the first conductive layer 6A, and on the other side the second and third conductive layers 10A, 12A.

As an alternative (not shown in the Figures), a stack of additional piezoelectric elements (e.g. 3, 4, 5, etc. . . . piezoelectric elements) with appropriate polarization and conductive layers connections can be made. Greater is the number of piezoelectric elements, the more signal is delivered by the stack, thus improving measurements that can be made with the sensor.

The piezoelectric element may have a plain cylindrical shape or a ring shape, namely cylindrical shape that is hollow in its center part.

Advantageously, the sensor further comprises any appropriate means for securing the sensor to a conduit, a tube or a pipe, e.g. flange, screw connection, etc. . . . (not shown in the Figures). Such means enables optimally positioning the resonating element within the fluid flow.

The piezoelectric element and compression assembly enable a reliable sensor behavior at high pressure and temperature (e.g. up to 30 Kpsi and 200 C) because:
- the piezoelectric element is working in compression and not in flexion, thus enabling high stress without failure;
- there is no glue involved in the assembly, thus giving high structure stability even at high temperature;
- there is low intrinsic losses, thus enabling achieving high quality factor required for low viscosity fluids measurements; and
- the piezoelectric efficiency losses are minimized, thus enabling high signal to noise ratio even at maximum pressure range.

Figure 2:
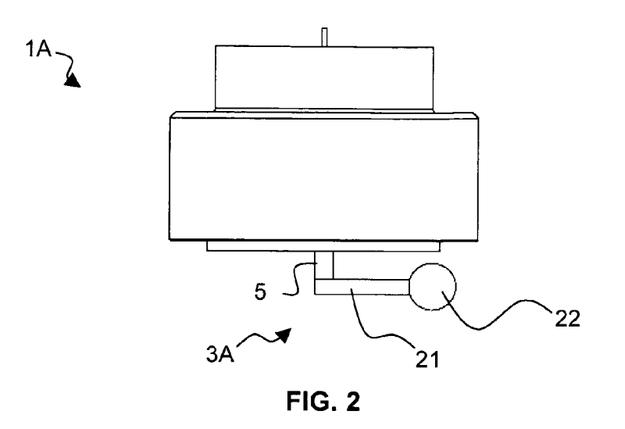
FIGS. 2, 3 and 4 are side, perspective and bottom views schematically showing a sensor for measuring density and viscosity of a fluid according to a first embodiment of the invention, respectively.
Figure 3:
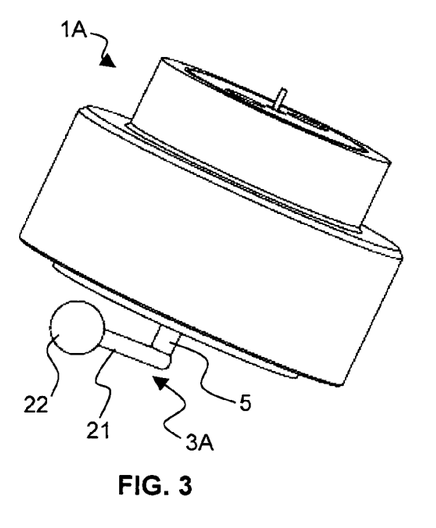
Figure 4:
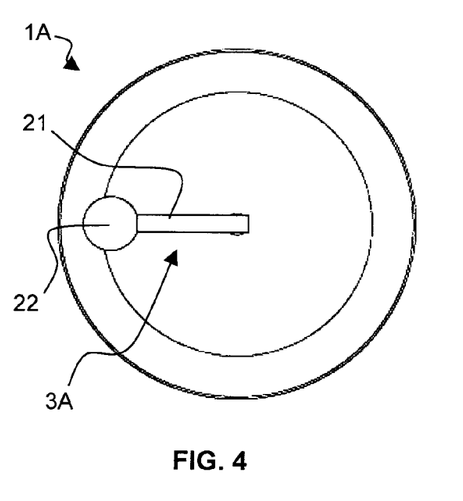

FIGS. 2, 3 and 4 are side, perspective and bottom views schematically showing a sensor for measuring density and viscosity of a fluid according to a first embodiment 1A of the invention, respectively. In this embodiment, the resonating element 3A is under the form of a beam 21, substantially straight, attached at one end to the housing 2 by the mechanical coupling element 5 and comprising, at the other end, a spherical mass 22. The beam 21 is made of a wire having a circular cross-section or an elliptical cross-section.

Figure 5:
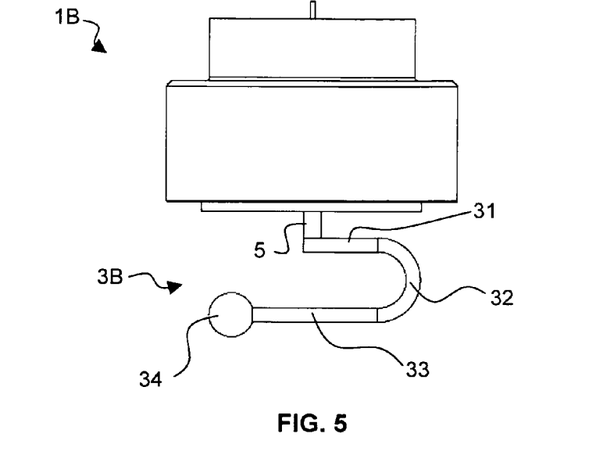
FIGS. 5, 6 and 7 are side, perspective and bottom views schematically showing a sensor for measuring density and viscosity of a fluid according to a second embodiment of the invention, respectively.
Figure 6:
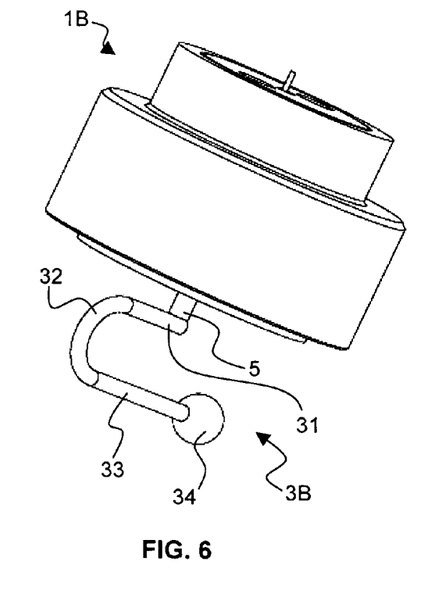
Figure 7:
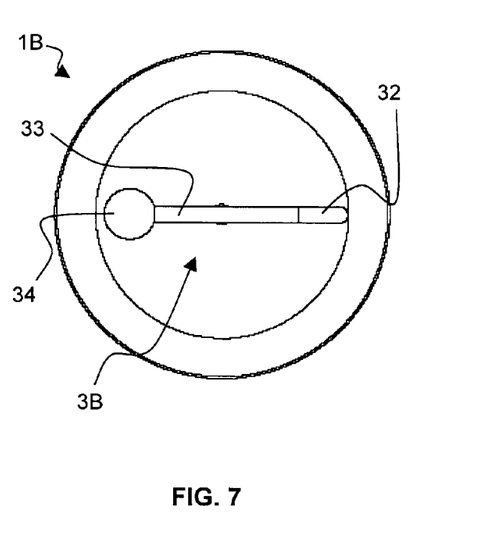

FIGS. 5, 6 and 7 are side, perspective and bottom views schematically showing a sensor for measuring density and viscosity of a fluid according to a second embodiment 1B of the invention, respectively. In this embodiment, the resonating element 3B is under the form of a non-symmetrical U beam comprising a suspended mass at one end. More precisely, the resonating element 3B comprises a first beam portion 31, a second beam portion 32 bent according to a U, a third beam portion 33. The first beam portion 31 and the third beam portion 33 are substantially straight. The beam portions are made of a wire having a circular cross-section or an elliptical cross-section. A spherical mass 34 is attached at the end of the third beam portion 33.

Figure 8:
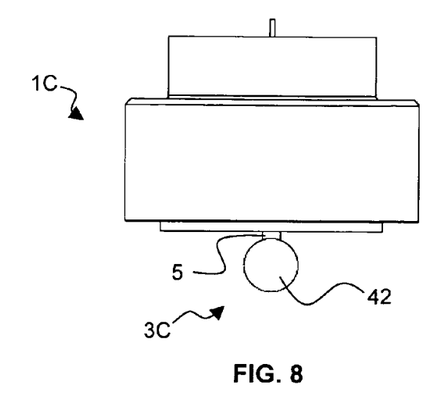
FIGS. 8, 9 and 10 are side, perspective and bottom views schematically showing a sensor for measuring density and viscosity of a fluid according to a third embodiment of the invention, respectively.
Figure 9:
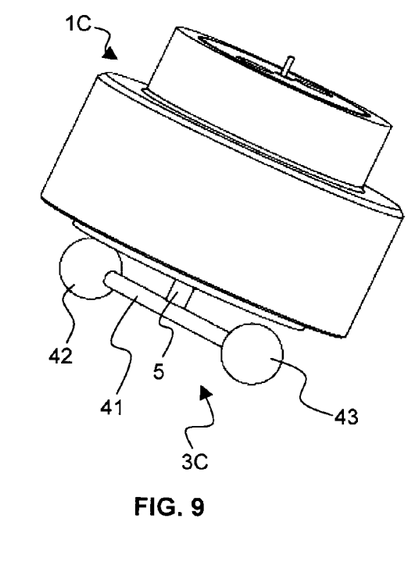
Figure 10:
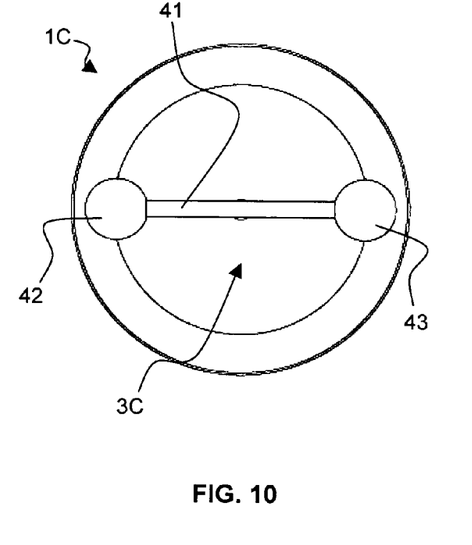

FIGS. 8, 9 and 10 are side, perspective and bottom views schematically showing a sensor for measuring density and viscosity of a fluid according to a third embodiment 1C of the invention, respectively. In this embodiment, the resonating element 3C is under the form of a beam 41, substantially straight, attached at its center to the housing 2 by the mechanical coupling element 5 and comprising, at the each end, a spherical mass 42 and 43. The beam 41 is made of a wire having a circular cross-section or an elliptical cross-section.

Figure 11:
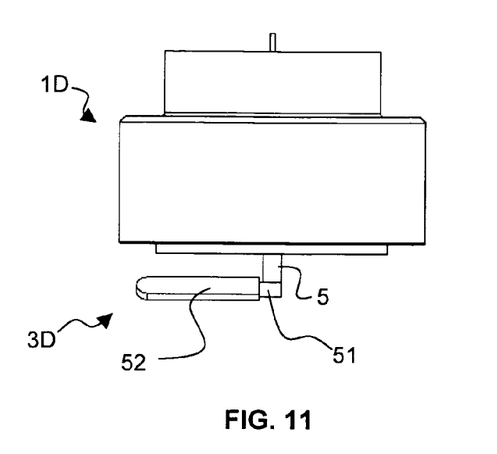
FIGS. 11, 12 and 13 are side, perspective and bottom views schematically showing a sensor for measuring density and viscosity of a fluid according to a fourth embodiment of the invention, respectively.
Figure 12:
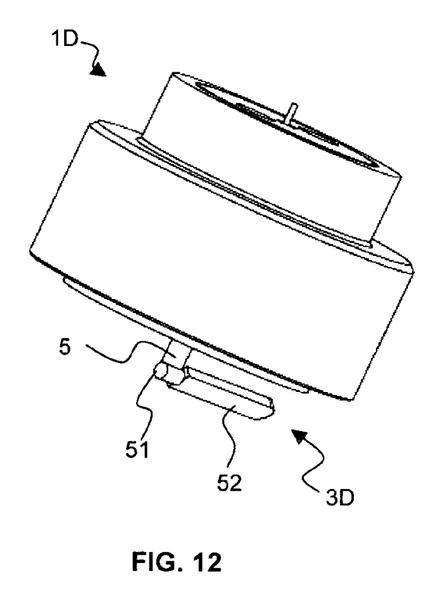
Figure 13:
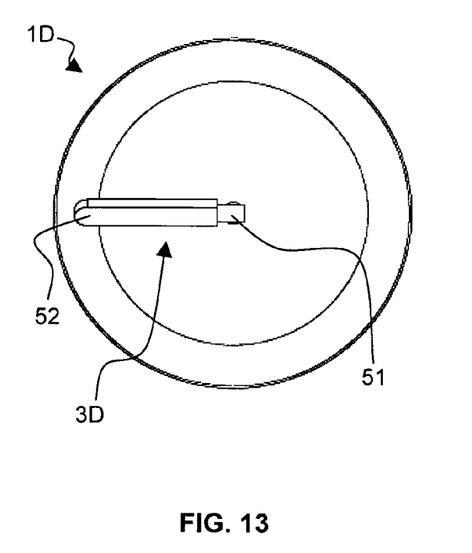

FIGS. 11, 12 and 13 are side, perspective and bottom views schematically showing a sensor for measuring density and viscosity of a fluid according to a fourth embodiment 1D of the invention, respectively. In this embodiment, the resonating element 3D comprises a straight connecting part 51 attached to the housing 2 by the mechanical coupling element 5 and, at one end, a paddle shape beam 52. The paddle shape beam 52 forms an angle (e.g. 45° but any other angles may be convenient) relatively to the direction defined by the mechanical coupling element 5 or relatively to the plane defined by the membrane.

Figure 14:
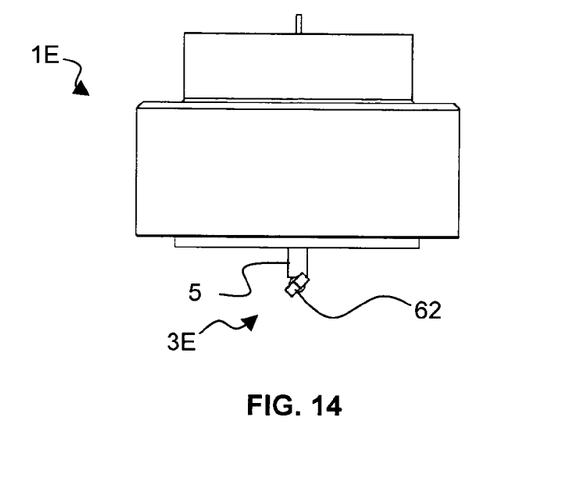
FIGS. 14, 15 and 16 are side, perspective and bottom views schematically showing a sensor for measuring density and viscosity of a fluid according to a fifth embodiment of the invention, respectively.
Figure 15:
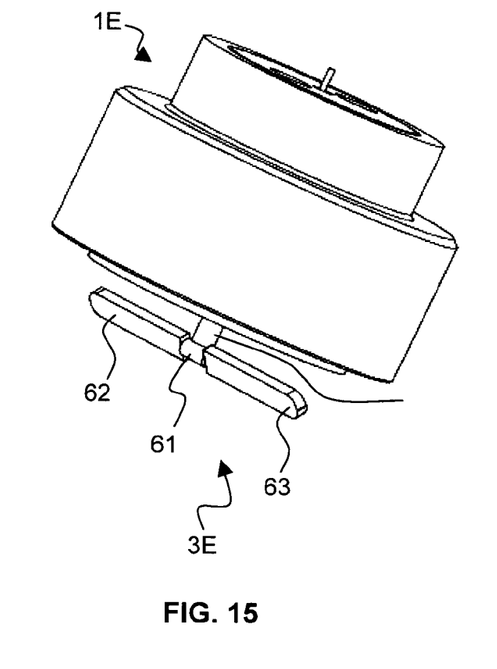
Figure 16:
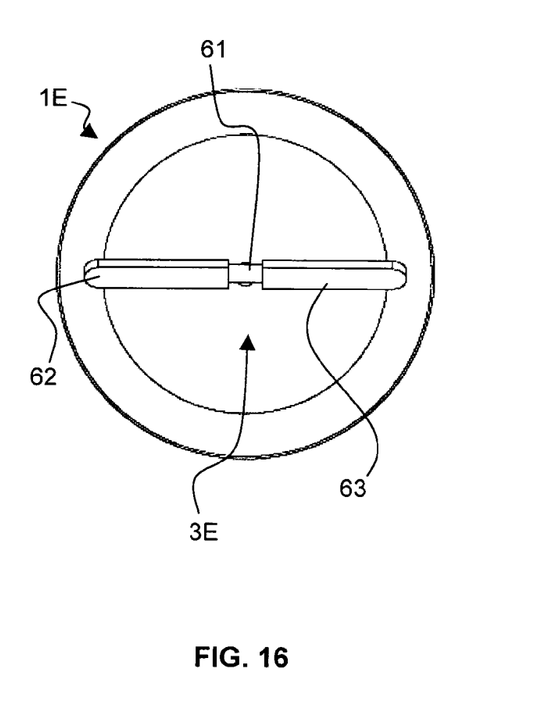

FIGS. 14, 15 and 16 are side, perspective and bottom views schematically showing a sensor for measuring density and viscosity of a fluid according to a fifth embodiment 1E of the invention, respectively. In this embodiment, the resonating element 3E comprises a straight connecting part 61 attached to the housing 2 by the mechanical coupling element 5 and, at each end, a first 62 and a second 63 paddle shape beam. The paddle shape beams 62, 63 form an angle (e.g. 45° but any other angles may be convenient) relatively to the direction defined by the mechanical coupling element 5 or relatively to the plane defined by the membrane. Both paddle shape beams may be oriented according to the same direction.

Figure 17:
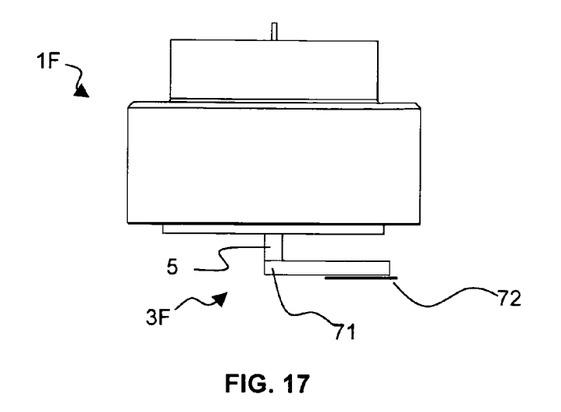
FIGS. 17, 18 and 19 are side, perspective and bottom views schematically showing a sensor for measuring density and viscosity of a fluid according to a sixth embodiment of the invention, respectively.
Figure 18:
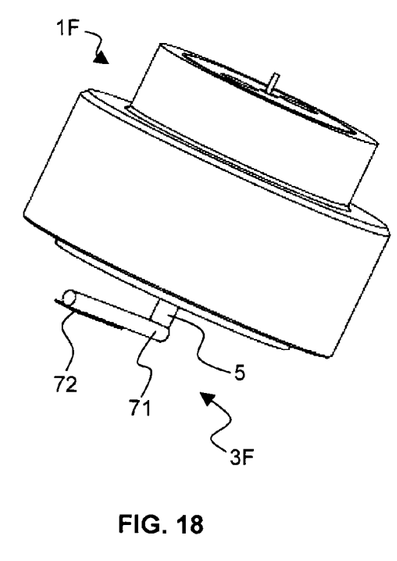
Figure 19:
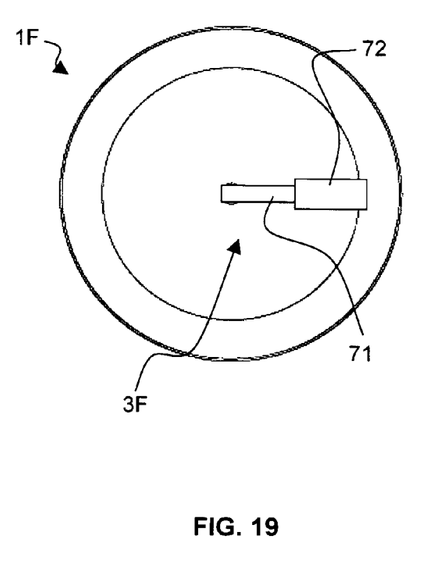

FIGS. 17, 18 and 19 are side, perspective and bottom views schematically showing a sensor for measuring density and viscosity of a fluid according to a sixth embodiment 1F of the invention, respectively. In this embodiment, the resonating element 3F is under the form of a beam 71, substantially straight, attached at one end to the housing 2 by the mechanical coupling element 5 and comprising, around the other end, a plate 72. The plate 72, substantially parallel to the plane defined by the membrane, is attached along the beam 71. The plate 72 may have a width greater than the beam diameter and may protrude at the end of the beam 72. The beam 71 is made of a wire having a circular cross-section or an elliptical cross-section.

Figure 20:
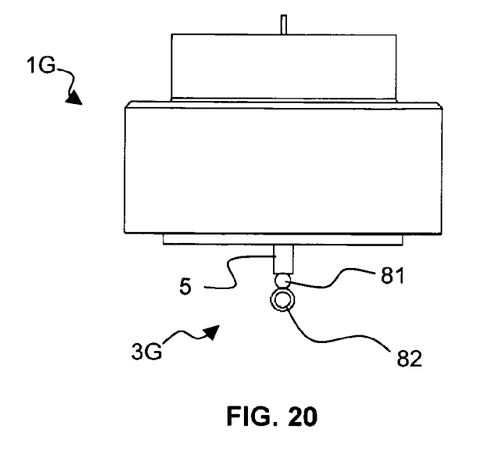
FIGS. 20, 21 and 22 are side, perspective and bottom views schematically showing a sensor for measuring density and viscosity of a fluid according to a seventh embodiment of the invention, respectively.
Figure 21:
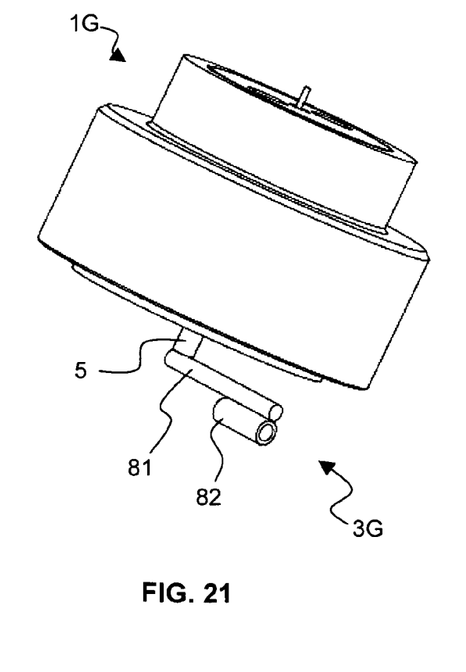
Figure 22:
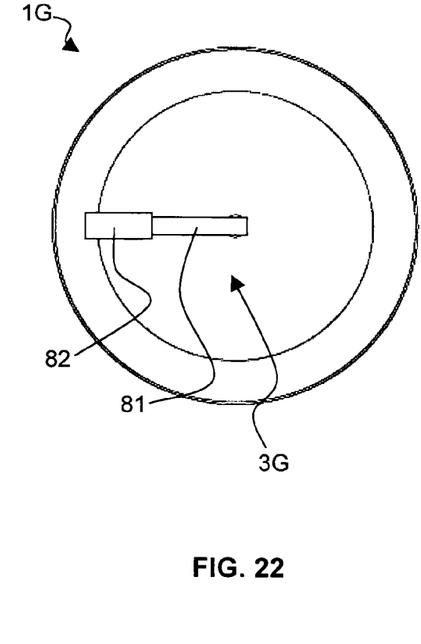

FIGS. 20, 21 and 22 are side, perspective and bottom views schematically showing a sensor for measuring density and viscosity of a fluid according to a seventh embodiment 1G of the invention, respectively. In this embodiment, the resonating element 3G is under the form of a beam 81, substantially straight, attached at one end to the housing 2 by the mechanical coupling element 5 and comprising, around the other end, a tube portion 82. The tube portion 82, substantially parallel to the plane defined by the membrane, is attached along the beam 81. The tube portion 82 may have a diameter greater than the beam diameter. The beam 81 is made of a wire having a circular cross-section or an elliptical cross-section.

Preferably, the resonating element according to any of the hereinbefore embodiment is aligned with the fluid flow. This configuration enables to minimize erosion effect in high velocity particles fluid. It also enables to minimize turbulences induced by the presence of the measuring device and thus the noise on the resonating element.

In the hereinbefore described embodiments, the various beams that can be seen in the Figures comprise wires having a circular cross-section. However, this is not limitative as the beams may alternatively comprise any wire having an elliptical cross-section or having a parallelepipedic cross-section (for example a rectangular cross-section) or having a triangular cross-section, etc. . . . The diameter or the width of the wire may be a few hundreds of micrometers.

Advantageously, the sensor elements in contact with the fluid, e.g. housing 2, membrane 9, coupling element 5, resonating element 3 are made of high strength and high corrosion resistance stainless steel, for example Inconel.

The resonating element can also be made of material with low density such as sapphire or boron carbon. The use of sapphire or boron carbon improves sensitivity to fluid density.

Alternatively, the resonating element can be made of specific materials for detecting or measuring chemical species in the fluid.

Figure 23:
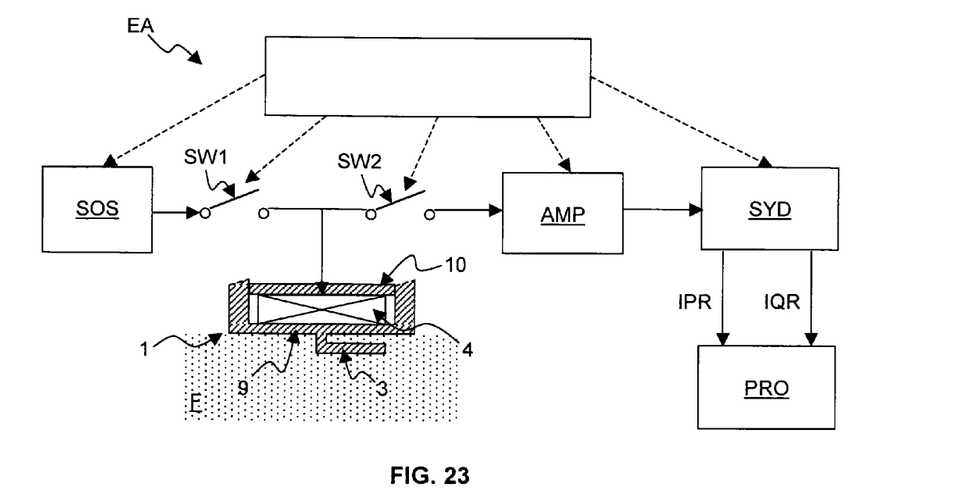
FIG. 23 schematically illustrates an electronic arrangement associated with the sensor of the invention.

FIG. 23 schematically illustrates an electronic arrangement EA associated with the density and viscosity sensor of the invention. The electronic arrangement may form an integral part with the density and viscosity sensor 1 by integration inside the chamber, or may be externally coupled to an external connector. The electronic arrangement may comprise discrete electronic components or may be implemented under the form of an integrated circuit.

The electronic arrangement EA comprises a controlling circuit LOG, an oscillator SOS, a first switch SW1, a second switch SW2, an amplifier AMP, a detection circuit SYS and a processing circuit PRO.

The controlling circuit LOG is coupled to the oscillator SOS, the first SW1 and second SW2 switch, the amplifier AMP and the detection circuit SYS.

The oscillator performs a sensor excitation and detection scheme that will be described in more details hereinafter.

In a first step, the controlling circuit LOG closes the first switch SW1 and opens the second switch SW2. Thus, the oscillator SOS applies an excitation signal to the piezoelectric element 4. The excitation signal application causes the piezoelectric element 4 to apply displacements to the coupling element and to the resonating element 3. The excitation signal is typically in the range of a few to a few hundred Volts depending of the excitation signals required.

Once the resonating element 3 has been put into vibration by exciting the piezoelectric element 3, the excitation could be removed and a reception signal representative of the vibration of the resonating element 3 in the fluid F can be measured.

Accordingly, in a second step, the controlling circuit LOG closes the second switch SW2 and opens the first switch SW1. Thus, the piezoelectric element generates a reception signal representative of the resonating element 3 vibration.

The detection signal is amplified by the amplifier AMP. The detection circuit SYS performs a synchronous detection during a detection phase. It provides to the processing circuit PRO, an actual in-phase response signal IPR and an actual quadrature response signal IQR measured by the sensor 1.

The processing circuit PRO provides the density and viscosity of the fluid F according to a density and viscosity determination method that will be described in more details hereinafter.

It is to be noted that the second switch SW2 may be omitted or replaced by an appropriate resistance. The second switch SW2 basic function is to protect the amplifier AMP because of the difference of magnitude order between the excitation signal and the reception signal.

In order to measure the frequency and quality factor of one vibrating mode the following excitation detection scheme is applied. It is based on the succession of an excitation phase followed by a waiting phase and a detection phase.

A broadband excitation signal covering the full range of possible resonance frequency, namely F0−ΔF to F0+ΔF, according to the range of operation of the sensor is applied through the switch SW1. For instance the excitation signal is based on a few periods of a sinus signal which frequency F0 is centered respectively with the useful frequency range, the number of periods defining the width of the useful spectrum. Advantageously the excitation signal stops when crossing zero.

After the waiting phase, for example a duration of one period, the decaying signal due to the oscillation amortization of the resonating element in the fluid is measured. The detection duration is a compromise between computing complexity and measurement accuracy. The order of magnitude is a few hundred of periods. The detection signal is amplified and multiplied by two reference signals, at a frequency near F0, and with 90° phase difference. In-phase and quadrature responses are obtained; these two responses are then applied to a low pass filter whose bandwidth is ΔF.

The resulting signals are then used to determine both resonance frequency and quality factor based on the parametrical identification method described in patent application EP05290502.3 incorporated herein by reference. The actual responses are compared to calculated response with various resonant frequencies, quality factors and associated correlation coefficient. The resonant frequency and the quality factor corresponds to a resonant frequency/quality factor pair which is associated with the higher normalized correlation coefficient sum that can be determined.

The excitation and detection scheme, together with the density and viscosity calculation according to the invention enables a drastic reduction of the time required to perform resonance frequency and quality factor measurement for un unknown fluid compared to the prior art sensor and method. For example, with the invention measurement and calculation can be performed in less than 1 second.

Based on the determined resonant frequency F and the quality factor Q and a fitting model for the particular resonating element used, the density $\eta$ and viscosity $\rho$ can be calculated. As the resonating element 3 vibrates in the fluid F, some of the surrounding fluid is displaced. The effective mass of the resonating element 3 is increased by an amount $\delta m$ determined by the volume and density of fluid entrained by the moving section. Consequently, this effect is related to fluid density, and a densitometer is provided.

As the resonating element 3 vibrates in the fluid F, the resonating element drags through the fluid in shear. Consequently, the vibration is dependent upon the resistance to shear of the fluid, and a viscometer is provided.

It is possible to sensibly determine an exact analytical modelling of the resonating element to fluid interaction.

The density $\rho$ equation is given by:

$$\rho = \rho_R \cdot \left(K \cdot \left(\frac{F_V}{F}\right)^2 - 1\right) \cdot \left(FIT0 + FIT1 \cdot \left(1 - \left(\frac{F}{F_V}\right)^2 \cdot \frac{1}{K}\right)^{-1} \cdot \left(\frac{1}{Q} - \frac{1}{Q_V}\right)\right) \quad [1]$$

The viscosity $\eta$ is given by:

$$\eta = \frac{\rho_R \cdot F_V^2 \cdot K \cdot R^2}{F \cdot \sqrt{K} \cdot \left(\frac{1}{Q} - \frac{1}{Q_V}\right)^{-2} \cdot \left(1 - \left(\frac{F}{F_V}\right)^2 \cdot \left(\frac{1}{K}\right)\right)} \cdot$$

$$\left(FIT2 + FIT3 \cdot \left(1 - \left(\frac{F_1}{F_V}\right) \cdot \frac{1}{K}\right)^{-1} \cdot \left(\frac{1}{Q_1} - \frac{1}{Q_V}\right)\right) \quad [2]$$

In these equations:

F and $F_V$ are the resonance frequency of the fluid currently measured and the resonance frequency in vacuum;

Q and $Q_V$ are the quality factors currently measured and quality factor in vacuum associated—in practice and depending on the targeted accuracy, the resonance frequency in vacuum may be replaced by the resonance frequency values measured in the air;

FIT0, FIT1, FIT2, FIT3 are the fitting parameters that are determined by measuring the resonance frequencies and quality factors in fluids of known density and viscosity;

$\rho_R$ is the density of the beam and R is the characteristic dimension of the beam;

the correction factor K is representing the shift of the young's modulus of the material (e.g. Inconel) forming the beam due to the variation of the pressure and the temperature with respect to the pressure and temperature condition when measuring $F_V$, $Q_V$. K is also affected by any shift in the electronics reference frequency due to temperature or ageing.

A key element of the invention is to replace the evaluation of K through independent measurement of temperature, pressure and the knowledge of beam material properties by using at least two vibration modes of a single vibrating element (or two vibrating beams of same material) having different fitting parameters. In the case of two modes, the correction factor K can be calculated writing that the first $\rho_1$ and second $\rho_2$ density measurements are equal. Therefore, stating $\rho_1 = \rho_2$ results in the following equation:

$$K = \frac{FIT10 - FIT20}{\left(\left(\frac{F_{1V}}{F_1}\right)^2 \cdot \left(FIT10 + FIT11 \cdot \left(\frac{1}{Q_1} - \frac{1}{Q_{1V}}\right)\right)\right) - \left(\left(\frac{F_{2V}}{F_2}\right)^2 \cdot \left(FIT20 + FIT21 \cdot \left(\frac{1}{Q_2} - \frac{1}{Q_{2V}}\right)\right)\right)} \quad [3]$$

where FIT10, FIT11, FIT20, FIT21 are fitting parameters that are determined by measuring the resonance frequencies and quality factors in fluids of known density and viscosity.

Similarly K can be computed using the two viscosities.

While K has been computed density and viscosity can be determined replacing K by its value in equation [1] and [2].

It has to be noted that equations [1] to [3] do not need input of temperature nor pressure representing fully compensated density and viscosity predictions based on a robust analytical model.

An example of a dual mode resonator is described below base on the fourth embodiment shown in FIGS. 11 to 13.

The resonating element is a paddle shaped beam having an angle with the axe of the excitation movement to allow excitation/detection of vibration modes in the plane of the paddle and perpendicularly to this plane.

The first resonance mode is characterized by a first resonant frequency $F_1$ and a first quality factor $Q_1$. This mode corresponds to the paddle oscillating perpendicularly to its plane. In this mode, the paddle moves a large volume of fluid. Consequently, the first resonant frequency $F_1$ is highly sensitive to fluid density. The second resonance mode is characterized by a second resonant frequency $F_2$ and a second quality factor $Q_2$. This mode corresponds to the paddle oscillating within its plane. In this mode, the paddle mostly shears the surrounding fluid. Consequently, the second resonant frequency $F_2$ is quite insensitive to fluid density while being sensitive to the damping effect.

Thus the fitting parameters are very different allowing the determination of K. Consequently, an accurate density and viscosity can be calculated.

Advantageously, all the above method steps are implemented by the processing circuit PRO of the electronic arrangement EA.

Final Remarks

An actuating/detecting element under the form of a piezoelectric element has been described. However, it will be apparent that this is an example of actuating/detecting element and that any electrical/mechanical vibration converting arrangement, e.g. a electrical motor, may be employed.

It will be apparent for a person skilled in the art, that the invention is not limited to the four particular resonating elements described hereinbefore. Provided that one can find the equation modeling the behavior of the resonating element 3 in a fluid, said element may have others shapes, for example a beam stretched between the two arms of a fork, etc. . . .

Further, the beams are shown in the Figures as sensibly parallel to the area of the sensor housing contacting the fluid to be measured. However, it will be apparent for a person skilled in the art that each beam may be positioned relatively to the area of the sensor housing contacting the fluid to be measured according to any angle (for example 10°, 30°, 45°, etc. . . . ).

The connection of the density and viscosity sensor to a conduit in which flow a fluid to be measured is not limited to the example hereinbefore described. It will be apparent for a person skilled in the art that others connections are possible depending of the application of the density and viscosity sensor.

Further, a plurality of sensors may be positioned in close proximity, for example two sensors may be positioned along the flow line for redundancy measurement purposes.

Also, the meaning of the term "connector" used in hereinbefore is not limited to a mechanical/electrical connection. It will be apparent for a person skilled in the art that a wireless connector may be used to transmit measurements from the sensor to any system requiring such measurements.

The invention finds application in various industry domains, for example the oilfield industry as density and viscosity sensor in down-hole tool, the chemical industry (plastic manufacturing, cosmetic preparation manufacturing), food industry, etc. . . . . It may also be employed in aeronautical applications, for example for detecting the formation of ice on e.g. plane wing by measuring the shift of resonance frequency due to the ice added mass on the resonating element.

The drawings and their description hereinbefore illustrate rather than limit the invention. Any reference sign in a claim should not be construed as limiting the claim. The word "comprising" does not exclude the presence of other elements than those listed in a claim. The word "a" or "an" preceding an element does not exclude the presence of a plurality of such element.

The invention claimed is:

1. A density and viscosity sensor for measuring density and viscosity of fluid, the sensor comprising:

a resonating element arranged to be immersed in the fluid, an actuating/detecting element coupled to the resonating element, a connector for coupling to the actuating/detecting element, a housing defining a chamber isolated from the fluid, the housing comprising an area of reduced thickness defining a membrane separating the chamber from the fluid, the membrane having a thickness enabling transfer of mechanical vibration between the actuating/detecting element and the resonating element, the actuating/detecting element is positioned within the chamber so as to be isolated from the fluid and mechanically coupled to the membrane, the resonating element arranged to be immersed in the fluid is mechanically coupled to the membrane, wherein the resonating element has a shape defining a first resonance mode and a second resonance mode characterized by different resonant frequencies ($F_1$,$F_2$) and different quality factors ($Q_1$,$Q_2$), the first resonance mode moving a volume of fluid, the second mode shearing a surrounding fluid.

2. A density and viscosity sensor according to claim 1, wherein the resonating element is mechanically coupled to the membrane by a mechanical coupling element and is chosen among the group of resonating elements comprising:

a beam, substantially straight, attached at one end to the coupling element and comprising, at the other end, a spherical mass, a non-symmetrical U beam comprising a spherical mass suspended at one end, a beam, substantially straight, attached at its center to the coupling element and comprising, at the each end, a spherical mass, a straight connecting part attached to the coupling element and comprising, at one end, a paddle shape beam, a straight connecting part attached to the coupling element and comprising, at each end, a first and a second paddle shape beam, a beam, substantially straight, attached at one end to the coupling element and comprising, around the other end, a plate, or a beam, substantially straight, attached at one end to the coupling element and comprising, around the other end, a tube portion.

3. A density and viscosity sensor according to claim 1, wherein the area of reduced thickness forms a cavity in which the actuating/detecting element is secured.

4. A density and viscosity sensor according to claim 1, wherein the sensor further comprises an electronic arrangement (EA) for driving the actuating/detecting element from an actuating mode into a detecting mode and vice-versa.

5. A density and viscosity sensor according to claim 1, wherein the resonating element comprises at least a part of the beam aligned with a flow direction of the fluid.

6. A density and viscosity sensor according to claim 1, wherein the first resonance mode moving a volume of fluid is highly sensitive to the density of the fluid, and the second resonance mode shearing the surrounding fluid is insensitive to the density of the fluid.

7. A density and viscosity sensor according to claim 6, wherein the first and second resonance modes are related to a single value of the density and viscosity of the fluid to be measured.

8. A density and viscosity sensor according to claim 1, wherein the actuating/detecting element comprises at least one piezoelectric element.

9. A density and viscosity sensor according to claim 8, wherein one of the at least one piezoelectric elements comprises a first and a second side, the first side being coupled to the connector by a connecting wire, the second side being electrically coupled to the membrane.

10. A density and viscosity sensor according to claim 8, wherein one of the at least one piezoelectric elements is pushed against the membrane through a compression assembly screwed into the cavity, said compression assembly comprising a hole for coupling to the connecting wire.

11. A density and viscosity sensor according to claim 10, wherein the compression assembly comprises a plug, a screwing plug and a supporting part.

12. A method for measuring density and viscosity of a fluid comprising the steps of:
  a) applying an excitation signal to a resonating arrangement comprising an actuating/detecting element and a resonating element arranged to be immersed in the fluid,
  b) detecting a reception signal provided by the resonating arrangement,
  c) determining an in-phase sensor actual response and a quadrature sensor actual response based on the reception signal detected,
  d) calculating an in-phase sensor model response and a quadrature sensor model response based on an initial resonant frequency and an initial quality factor of the resonating element,
  e) comparing the in-phase sensor model response to the in-phase sensor actual response, and the quadrature sensor model response to the quadrature sensor actual response by determining an associated correlation coefficient,
  f) repeating the calculating step and the comparing step with a modified resonant frequency and a modified quality factor and memorizing a determined number of resonant frequency, quality factor and associated correlation coefficient, and
  g) determining a resulting resonant frequency and a resulting quality factor of the resonating element in the fluid based on the determined number of associated correlation coefficient,
  wherein the resulting resonant frequency and the resulting quality factor of the resonating element are determined according to a first resonance mode and a second resonance mode of the resonating element characterized by a different first ($F_1$) and second ($F_2$) resonant frequency and a different first ($Q_1$) and second ($Q_2$) quality factors, the first resonance mode moving a volume of fluid, the second mode shearing a surrounding fluid, and
  h) determining density and viscosity of the fluid based on the first ($F_1$) and second ($F_2$) resonant frequency and the first ($Q_1$) and second ($Q_2$) quality factors and a plurality of fitting parameters that are determined by measuring the resonance frequencies and quality factors in fluids of known density and viscosity.

13. A density and viscosity measuring method according to claim 12, wherein the excitation signal is a broadband excitation signal including the different resonant frequencies ($F_1$, $F_2$).

14. A density and viscosity measuring method according to claim 12, wherein the excitation signal swept a range of frequency including the different resonant frequencies ($F_1$, $F_2$).

15. A density and viscosity measuring method according to claim 12, wherein the comparison and resonant frequency/quality factor determination steps are based on a parametrical identification.

16. A density and viscosity measuring method according to claim 12, wherein the first resonance mode moving a volume of fluid is highly sensitive to the density of the fluid, and the second resonance mode shearing the surrounding fluid is insensitive to the density of the fluid.

17. A density and viscosity measuring method according to claim 16, wherein the first and second resonance modes are related to a single value of the density and viscosity of the fluid to be measured.

* * * * *